(12) United States Patent
Maeta et al.

(10) Patent No.: US 9,045,573 B2
(45) Date of Patent: Jun. 2, 2015

(54) SOLID-PHASE SUPPORT FOR OLIGONUCLEOTIDE SYNTHESIS AND OLIGONUCLEOTIDE SYNTHESIS METHOD

(71) Applicant: Nitto Denko Corporation, Ibaraki-shi, Osaka (JP)

(72) Inventors: Eri Maeta, Ibaraki (JP); Kenjiro Mori, Ibaraki (JP); Kazuya Miwa, Ibaraki (JP)

(73) Assignee: Nitto Denko Corporation, Ibaraki (JP)

( * ) Notice: Subject to any disclaimer, the term of this patent is extended or adjusted under 35 U.S.C. 154(b) by 114 days.

(21) Appl. No.: 13/901,266

(22) Filed: May 23, 2013

(65) Prior Publication Data
US 2013/0317206 A1 Nov. 28, 2013

(30) Foreign Application Priority Data
May 23, 2012 (JP) ................................. 2012-118041

(51) Int. Cl.
| C07H 21/00 | (2006.01) |
| C08F 22/10 | (2006.01) |
| C07H 19/06 | (2006.01) |
| C07H 19/16 | (2006.01) |
| C07H 19/04 | (2006.01) |
| C07B 35/04 | (2006.01) |
| C08F 212/36 | (2006.01) |
| C07B 61/00 | (2006.01) |
| C08F 212/08 | (2006.01) |
| C07H 21/04 | (2006.01) |
| C08F 12/22 | (2006.01) |
| C08F 2/18 | (2006.01) |

(52) U.S. Cl.
CPC .............. *C08F 22/105* (2013.01); *C07H 19/06* (2013.01); *C07H 19/16* (2013.01); *C07H 19/04* (2013.01); *C07B 35/04* (2013.01); *C08F 212/36* (2013.01); *C07B 61/02* (2013.01); *C08F 12/22* (2013.01); *C08F 212/08* (2013.01); *C08F 2/18* (2013.01); *C07H 21/04* (2013.01); *C08F 2800/20* (2013.01)

(58) Field of Classification Search
None
See application file for complete search history.

(56) References Cited

U.S. PATENT DOCUMENTS

| 5,047,524 A | 9/1991 | Andrus et al. |
| 7,115,672 B2 | 10/2006 | Mori et al. |
| 2005/0256285 A1 | 11/2005 | Mori et al. |
| 2009/0291294 A1 | 11/2009 | Mori et al. |
| 2009/0326210 A1 | 12/2009 | Mori et al. |
| 2012/0010396 A1 | 1/2012 | Mori et al. |

FOREIGN PATENT DOCUMENTS

| EP | 0496405 A1 * | 7/1992 | ............ C08F 212/14 |
| JP | H03-068593 A | 3/1991 | |
| JP | 2005-325272 A | 11/2005 | |
| JP | 2008-074979 A | 4/2008 | |

OTHER PUBLICATIONS

Miyoshi et al. Nucleic Acid Research (1980), vol. 8, pp. 5473-5490.*
European Patent Office, Extended European Search Report in European Patent Application No. 13168561.2 (Aug. 1, 2013).

* cited by examiner

*Primary Examiner* — Patrick Lewis
(74) *Attorney, Agent, or Firm* — Leydig, Voit & Mayer, Ltd.

(57) ABSTRACT

The present invention provides a solid-phase support for oligonucleotide synthesis for synthesizing long chain oligonucleotide, RNA oligonucleotide and modified oligonucleotide at high synthetic quantity and high purity with a low loading amount of a linker. Provided is a solid-phase support for oligonucleotide synthesis comprising a porous resin bead having a monovinyl monomer unit, a crosslinkable vinyl monomer unit and a polyethylene glycol unit and a cleavable linker loaded on its surface,
the porous resin bead having a group capable of binding to a carboxy group by a dehydration condensation reaction on its surface, the cleavable linker having a carboxy group, wherein the carboxy group of the cleavable linker is bound to the group capable of binding to a carboxy group, by a dehydration condensation reaction, and
a loading amount of the cleavable linker is 1 to 80 μmol/g relative to the weight of the porous resin bead.

16 Claims, No Drawings

SOLID-PHASE SUPPORT FOR OLIGONUCLEOTIDE SYNTHESIS AND OLIGONUCLEOTIDE SYNTHESIS METHOD

CROSS-REFERENCE TO A RELATED APPLICATION

This patent application claims the benefit of Japanese Patent Application No. 2012-118041, filed May 23, 2012, which is incorporated herein by reference in its entirety.

TECHNICAL FIELD OF THE INVENTION

The present invention relates to a solid-phase support for oligonucleotide synthesis. More specifically, the present invention relates to a solid-phase support for oligonucleotide synthesis which is obtained by loading a cleavable linker on a porous resin bead comprised of a monovinyl monomer unit and a crosslinkable vinyl monomer unit, which bead has, on its surface, a group capable of binding to a carboxy group by a dehydration condensation reaction, and is bound with a polyethylene glycol unit.

BACKGROUND OF THE INVENTION

A solid-phase synthesis method which uses the phosphoramidite method is broadly used in the chemical synthesis of oligonucleotide. In this method, for example, a nucleoside which becomes the 3'-terminal of the oligonucleotide to be synthesized is firstly loaded in advance on a solid-phase support via a cleavable linker such as succinyl group, and this support is put into a reaction column and set on an automatic oligonucleotide synthesizer. Thereafter, synthesizing reagents are fed into the reaction column, for example, in the following manner in accordance with the synthesizing program of the automatic oligonucleotide synthesizer. (1) Deprotection of nucleoside 5'-OH group by a trichloroacetic acid/dichloromethane solution, dichloroacetic acid/toluene solution or the like, (2) coupling reaction of amidite with the 5'-OH group by a nucleoside phosphoramidite (nucleoside monomer)/acetonitrile solution and an activator (tetrazole or the like)/acetonitrile solution, (3) capping of the unreacted 5'-OH group by acetic anhydride/pyridine/methyl imidazole/THF or the like, and (4) oxidation of phosphite by iodine/water/pyridine or the like.

By repeating this synthesis cycle, oligonucleotide having the intended sequence is synthesized. The finally synthesized oligonucleotide is cut out from the solid-phase synthesis support by hydrolyzing the cleavable linker with ammonia, methylamine or the like (cf. non-patent document 1).

As the solid-phase support to be used in the oligonucleotide synthesis, inorganic particles such as CPG (Controlled Pore Glass), silica gel and the like have so far been used, but in recent years, resin beads which can increase quantity of oligonucleotide synthesized per weight of solid-phase support have been started to be used for synthesis at a moderate price and in a large quantity. As such resin beads, a highly-crosslinked and non-swelling porous polystyrene bead (cf. patent document 1), a low-crosslinked and swelling porous polystyrene bead (cf. patent document 2) and the like can for example be mentioned.

Generally, a longer oligonucleotide chain synthesized problematically causes lower synthesizability (synthetic purity and synthetic quantity). To solve this, it is necessary to decrease the loading amount of a nucleoside linker to be the origin of the synthesis of a solid-phase support. For example, DNA oligonucleotide containing 20 bases can be synthesized with high purity by using a commercially available porous resin bead solid-phase support having a nucleoside linker loading amount of about 200 μmol/g. However, in the case of a DNA oligonucleotide containing 40 bases, the amount needs to be 80 μmol/g or less. Also, when an RNA oligonucleotide or a modified oligonucleotide is to be synthesized, since amidite containing a bulky protecting group or modifying group is coupled, the oligonucleotide is synthesized using a lower loading amount of a nucleoside linker to prevent the synthesizability from decreasing.

However, when an oligonucleotide is synthesized using a porous resin bead as a solid-phase support for oligonucleotide synthesis, and a decreased laoding amount of a nucleoside linker, unexpectedly, the synthesizability problematically becomes lower than expected.

DOCUMENT LIST

Patent Documents patent document 1: JP-A-H3-68593
patent document 2: JP-A-2005-325272
patent document 3: JP-A-2008-74979

Non-Patent Document non-patent document 1: Current Protocol in Nucleic Acid Chemistry (2000), UNIT 3.6 Synthesis of Unmodified Oligonucleotide

SUMMARY OF THE INVENTION

Problems to be Solved by the Invention

The present invention aims to provide a solid-phase support for oligonucleotide synthesis affording a high synthetic quantity and high purity. Particularly, the present invention aims to provide a solid-phase support for synthesizing a long chain oligonucleotide, RNA oligonucleotide or modified oligonucleotide with a low loading amount of a linker.

Means of Solving the Problems

The present inventors have conducted intensive studies in view of the above-mentioned problem, and found that a long chain oligonucleotide, RNA oligonucleotide or modified oligonucleotide can be synthesized with high synthesizability (high synthetic purity and synthetic quantity) even with a low loading amount of a linker, by binding a polyethylene glycol unit to a porous resin bead for a solid-phase support for oligonucleotide synthesis, which resulted in the completion of the present invention.

Accordingly, the present invention is summarized as follows.

(1) A solid-phase support for oligonucleotide synthesis comprising a porous resin bead having a monovinyl monomer unit, a crosslinkable vinyl monomer unit and a polyethylene glycol unit and a cleavable linker loaded on its surface, the porous resin bead having a group capable of binding to a carboxy group by a dehydration condensation reaction on its surface, the cleavable linker having a carboxy group, wherein the carboxy group of the cleavable linker is bound to the group capable of binding to a carboxy group, by a dehydration condensation reaction, and a loading amount of the cleavable linker is 1 to 80 μmol/g relative to the weight of the porous resin bead.

(2) The solid-phase support for oligonucleotide synthesis of (1), wherein the monovinyl monomer unit comprises a styrene monomer unit.

(3) The solid-phase support for oligonucleotide synthesis of (1) or (2), wherein the number average molecular weight of the polyethylene glycol unit is 100 to 10000 and the binding amount thereof is 0.001 to 1 mmol/g relative to the weight of the porous resin bead.

(4) The solid-phase support for oligonucleotide synthesis of any of (1) to (3), wherein the group capable of binding to a carboxyl group comprises a hydroxy group or an amino group, and is covalently bonded to the cleavable linker having a carboxyl group.

(5) A method of synthesizing oligonucleotide, comprising successively binding nucleoside or nucleotide via the cleavable linker by using the solid-phase support for oligonucleotide synthesis of any of (1) to (4) to give an oligonucleotide.

Effect of the Invention

Even when synthesizing long chain oligonucleotide, RNA oligonucleotide and the like with a low loading amount of a linker, since the solid-phase support for oligonucleotide synthesis of the present invention affords oligonucleotide with high synthetic quantity and high synthetic purity, oligonucleotide can be synthesized more efficiently using the porous resin beads of the present invention, than using solid-phase support for oligonucleotide synthesis using conventional porous resin beads.

DESCRIPTION OF EMBODIMENTS

The monovinyl monomer unit, which is one of the structural units of the solid-phase support for oligonucleotide synthesis of the present invention, is not particularly limited as long as it is a monomer having one vinyl group in a molecule. Examples thereof include aromatic vinyl monomer, alkyl(meth)acrylate, vinyl acetate, (meth)acrylonitrile, vinylpyridine, vinylpyrrolidone and the like.

Examples of the aromatic vinyl monomer include a 5- or 6-membered aromatic ring having one vinyl group in a molecule, which optionally contains, besides carbon as a ring-constituting atom, a hetero atom such as a nitrogen atom and the like. The aromatic ring optionally has substituent(s) such as a halogen atom (e.g., a fluorine atom, a chlorine atom, a bromine atom, an iodine atom and the like), a straight chain or branched chain alkoxy group having 1 to 10 carbon atoms (e.g., a methoxy group, an ethoxy group and the like), a straight chain or branched chain alkyl group having 1 to 10 carbon atoms (e.g., a methyl group, an ethyl group and the like, said alkyl group is optionally substituted by a halogen atom, alkoxy group and the like), a straight chain or branched chain acyloxy group having 2 to 10 carbon atoms (e.g., an acetoxy group and the like), an amino group, a straight chain or branched chain acylamino group having 2 to 10 carbon atoms (e.g., an acetylamino group and the like), a cyano group, a nitro group and the like. Specific examples thereof include styrene monomers such as styrene, alkylstyrenes (ethylstyrene, methylstyrene, dimethylstyrene, trimethylstyrene, butylstyrene and the like), halogenated styrenes (chlorostyrene, dichlorostyrene, fluorostyrene, pentafluorostyrene, bromostyrene and the like), haloalkylstyrenes (chloromethylstyrene, fluoromethylstyrene and the like), aminostyrene, cyanostyrene, methoxystyrene, ethoxystyrene, butoxy styrene, acetoxystyrene, nitrostyrene and the like.

Examples of the alkyl(meth)acrylate include an ester obtained from a straight chain or branched chain monovalent alcohol wherein the alkyl group has 1 to 20 carbon atoms and acrylic acid or methacrylic acid, and the like. Said alcohol is optionally substituted by a halogen atom, a hydroxy group, an alkoxy group, an epoxy group, a phenyl group and the like. It also includes an ester obtained from polyethylene glycol, polyethylene glycol monoalkyl ether such as polyethylene glycol monomethyl ether etc., and the like, and acrylic acid or methacrylic acid, and the like. Specific examples thereof include methyl acrylate, butyl acrylate, 2-ethylhexyl acrylate, 2-hydroxyethyl acrylate, methoxyethyleneglycol acrylate, polyethylene glycol methyl ether acrylate, methyl methacrylate, ethyl methacrylate, butyl methacrylate, hexyl methacrylate, 2-ethylhexyl methacrylate, glycidyl methacrylate, stearyl methacrylate, 2-hydroxyethyl methacrylate, methoxyethyleneglycol methacrylate, polyethylene glycol methyl ether methacrylate, polyethylene glycol methacrylate, benzyl methacrylate, trifluoroethyl methacrylate, octafluoropentyl methacrylate and the like. The monovinyl monomer can be used alone or in a mixture of different ones.

The monovinyl monomer is preferably a styrene monomer, or a mixture of a styrene monomer and other monovinyl monomer.

The crosslinkable vinyl monomer, which is one of the structural units of the solid-phase support for oligonucleotide synthesis of the present invention, is one that can be used as a crosslinking agent, and is not particularly limited as long as it has two or more, preferably 2 or 3, vinyl groups in a molecule and can form a crosslinked network structure with the aforementioned monovinyl monomer. Examples thereof include divinylbenzene, trivinylbenzene, trivinylcyclohexane, ethyleneglycol di(meth)acrylate, diethyleneglycol di(meth)acrylate, triethyleneglycol di(meth)acrylate, more ploymeric ethyleneglycol di(meth)acrylate, propyleneglycol di(meth)acrylate, dipropyleneglycol di(meth)acrylate, tripropyleneglycol di(meth)acrylate, more polymeric propyleneglycol di(meth)acrylates, butanediol di(meth)acrylate, hexanediol di(meth)acrylate, nonanediol di(meth)acrylate and the like.

The crosslinkable vinyl monomer can be used alone or in a mixture of different ones. The crosslinkable vinyl monomer is particularly preferably p-divinylbenzene, m-divinylbenzene, or a mixture thereof.

The crosslinkable vinyl monomer unit of the porous resin beads of the present invention is 100 to 5000 μmol/g, preferably 300 to 3000 μmol/g, as the amount per the weight of the porous resin beads. When the crosslinkable vinyl monomer unit is less than 100 μmol/g, the obtained particles do not show sufficient solvent resistance, heat stability or porosity, and are not expected to show a desired effect when used as a solid-phase support for oligonucleotide synthesis. Conversely, when the unit exceeds 5000 μmol/g, since the swellability thereof in an organic solvent will decrease, the synthetic purity and synthetic quantity of the oligonucleotide obtained using the particles as a solid-phase support for oligonucleotide synthesis tend to decrease.

The "group capable of binding to a carboxy group by a dehydration condensation reaction" which is present on the surface of the porous resin beads is not particularly limited as long as it can form a bond with a carboxy group by a dehydration condensation reaction. It is preferably a group containing a hydroxy group or an amino group, and specific examples thereof include a hydroxy group, an amino group, a hydroxy-$C_{1-20}$ alkyl group such as a hydroxymethyl group and the like, an amino-$C_{1-20}$ alkyl group such as aminomethyl etc., and the like.

The group capable of binding to a carboxy group by a dehydration condensation reaction can be introduced onto the surface of the porous resin beads by (1) copolymerizing a vinyl monomer containing a group capable of binding to a carboxy group by a dehydration condensation reaction with the above-mentioned monovinyl monomer and crosslinkable vinyl monomer, or (2) copolymerizing a vinyl monomer containing a group convertible, by a reaction such as hydrolysis and the like, to a group capable of binding to a carboxy group by a dehydration condensation, with the above-mentioned monovinyl monomer and crosslinkable vinyl monomer, and thereafter subjecting the copolymer to a reaction such as hydrolysis and the like. The production methods thereof are described in detail later.

In the solid-phase support for oligonucleotide synthesis of the present invention, the polyethylene glycol unit possessed by the porous resin beads is not particularly limited as long as it has a polyethylene glycol structure ($-(CH_2CH_2O)_n-$ wherein n is an integer of 2 or more). The binding pattern of the polyethylene glycol unit and porous resin beads is not particularly limited, and includes ester bond, ether bond, amide bond and the like.

For binding a polyethylene glycol unit to the solid-phase support for oligonucleotide synthesis of the present invention, a method of copolymerizing vinyl monomers containing a polyethylene glycol unit, for example, polyethylene glycol methyl ether acrylate, polyethylene glycol phenyl ether acrylate, polyethylene glycol acrylate, polyethylene glycol methyl ether methacrylate, polyethylene glycol phenyl ether methacrylate, polyethylene glycol methacrylate and the like, can be mentioned.

As other method of binding a polyethylene glycol unit to the solid-phase support for oligonucleotide synthesis of the present invention, porous resin beads may be once synthesized by suspension copolymerization and the like, and then a polyethylene glycol unit may be introduced. For example, the binding can be performed by reacting porous resin beads, introduced with a chloromethyl group by copolymerizing chloromethylstyrene and the like, with polyethylene glycol oligomer such as polyethylene glycol, polyethylene glycol monomethyl ether, polyethylene glycol monophenyl ether and the like. Alternatively, the binding can be performed by binding porous resin beads, introduced with a functional group such as a carboxy group, an amino group, a hydroxy group, a glycidyl group and the like, to polyethylene glycol, polyethylene glycol biscarboxymethyl ether, polyethylene glycol bisamine, polyethylene glycol bis 3-aminopropyl, polyethylene glycol glycidyl and the like, by using a condensing agent and the like.

The number average molecular weight of the polyethylene glycol unit to be bonded to the solid-phase support for oligonucleotide synthesis of the present invention is 100 to 10000, preferably 150 to 5000, more preferably 200 to 3000, further preferably 200 to 2000.

When the number average molecular weight of the polyethylene glycol unit is lower than this range, the degree of hydrophilization on the support surface becomes low, and therefore, oligonucleotide synthesizability tends to decrease when the loading amount of the linker is low. Conversely, when it exceeds this range, the oligonucleotide synthesizability tends to become low, since the polyethylene glycol unit does not bind to the support easily or the polyethylene glycol unit inhibits oligonucleotide synthesis.

The number average molecular weight of the polyethylene glycol unit can be measured by gel permeation chromatography (GPC) method using high performance liquid chromatography. In addition, a commercially available product containing a polyethylene glycol unit having a desired number average molecular weight can be used.

When vinyl monomers containing a polyethylene glycol unit are copolymerized, the number average molecular weight of the vinyl monomer itself can be used as the number average molecular weight of the polyethylene glycol unit.

The binding amount of the polyethylene glycol unit to be bonded to the solid-phase support for oligonucleotide synthesis of the present invention is 0.001 to 1 mmol/g, preferably 0.005 to 0.7 mmol/g, more preferably 0.01 mmol/g to 0.6 mmol/g, relative to the weight of the porous resin beads in the solid-phase support.

When the binding amount of the polyethylene glycol unit is lower than this range, the degree of hydrophilization on the support surface becomes low, and therefore, oligonucleotide synthesizability tends to decrease when the loading amount of the linker is low. Conversely, when it exceeds this range, the oligonucleotide synthesizability tends to become low, since the polyethylene glycol unit inhibits oligonucleotide synthesis.

The binding amount of the polyethylene glycol unit relative to the weight of the porous resin beads can be determined by adjusting the amount of the vinyl monomer containing a polyethylene glycol unit or a functional group (a chloromethyl group, a carboxy group, an amino group, a hydroxy group, a glycidyl group etc.) on porous resin beads for the introduction of a polyethylene glycol unit.

The solid-phase support for oligonucleotide synthesis of the present invention does not need to always show a strict spherical shape, and only needs to have at least a granular shape. However, the solid-phase support for oligonucleotide synthesis of the present invention preferably has a spherical shape since the efficiency of packing a solid-phase synthesis reaction column can be enhanced and it is not easily broken.

While the median particle diameter of the solid-phase support for oligonucleotide synthesis of the present invention, which is measured by a laser diffraction scattering method, is not particularly limited, it is preferably from 1 to 1,000 µm, more preferably from 10 to 500 µm, further preferably from 20 to 300 µm. The median particle diameter of the porous resin bead of the present invention is measured by a laser diffraction scattering method. Specifically, average particle diameter is calculated by measuring it by a laser diffraction scattering type particle size distribution analyzer LA-950 (manufactured by Horiba, Ltd.) using 50% v/v ethanol aqueous solution as the dispersion medium.

The median particle diameter depends on the stirring condition before the commencement of polymerization in case of suspension polymerization for producing porous resin beads of solid-phase support for oligonucleotide synthesis, kind and concentration of the dispersion stabilizer. Accordingly, by adjusting these conditions, it is possible to adjust the median particle diameter within a desired range.

While the median pore diameter of the solid-phase support for oligonucleotide synthesis of the present invention, which is measured by a mercury intrusion method is not particularly limited, it is preferably from 1 to 1,000 nm, more preferably from 5 to 500 nm, further preferably from 10 to 300 nm.

The median pore diameter of the porous resin beads of the present invention is determined by mercury intrusion method. Specifically, 0.2 g of porous resin beads are placed in the mercury porosimeter PoreMaster 60-GT (manufactured by QuantaChrome Co.), and measurements are performed by the mercury intrusion method under the condition of a mercury contact angle of 140° and a mercury surface tension of 480 dyn/cm.

The median pore diameter depends on the stirring condition before the commencement of polymerization in case of suspension polymerization for producing porous resin beads of solid-phase support for oligonucleotide synthesis, kind and concentration of the porogen. Accordingly, by adjusting these conditions, it is possible to adjust the median pore diameter within a desired range.

The production method of the solid-phase support for oligonucleotide synthesis of the present invention is not particularly limited. Examples thereof include (1) a method of production using porous resin beads produced by mixing and dissolving a monovinyl monomer, a crosslinkable vinyl monomer, a vinyl monomer containing a group capable of binding to a carboxy group by a dehydration condensation reaction and a monomer that binds a polyethylene glycol unit, with a porogen and a polymerization initiator, and suspension-copolymerizing the mixture in water containing a dispersion stabilizer dispersed or dissolved therein, (2) a method of production using porous resin beads produced by mixing and dissolving a monovinyl monomer, a crosslinkable vinyl monomer, a vinyl monomer containing a group capable of binding to a carboxy group by a dehydration condensation reaction, and a vinyl monomer containing a functional group (chloromethyl group, carboxy group, amino group, hydroxy group, glycidyl group etc.), with a porogen and a polymerization initiator, suspension-copolymerizing the mixture in water containing a dispersion stabilizer dispersed or dissolved therein to synthesize porous resin beads, and introducing a polyethylene glycol unit by reaction with the functional group, (3) a method of production using porous resin beads produced by mixing and dissolving a monovinyl monomer, a crosslinkable vinyl monomer, a vinyl monomer containing a group convertible, by a reaction such as hydrolysis and the like, to a group capable of binding to a carboxy group by a dehydration condensation, and a monomer which binds a polyethylene glycol unit, with a porogen and a polymerization initiator, suspension-copolymerizing the mixture in water containing a dispersion stabilizer dispersed or dissolved therein, and the like, to synthesize porous resin beads, and introducing, by a reaction such as hydrolysis and the like, a group capable of binding to a carboxy group by a dehydration condensation reaction, (4) a method of production using porous resin beads produced by mixing and dissolving a monovinyl monomer, a crosslinkable vinyl monomer, a vinyl monomer containing a group convertible, by a reaction such as hydrolysis and the like, to a group capable of binding to a carboxy group by a dehydration condensation, and a vinyl monomer containing a functional group (chloromethyl group, carboxy group, amino group, hydroxy group, glycidyl group etc.), with a porogen and a polymerization initiator, suspension-copolymerizing the mixture in water containing a dispersion stabilizer dispersed or dissolved therein, and the like, to synthesize porous resin beads, introducing, by a reaction such as hydrolysis and the like, a group capable of binding to a carboxy group by a dehydration condensation reaction, and further introducing a polyethylene glycol unit by a reaction with a functional group, and the like.

In the suspension copolymerization, the amount of the crosslinkable vinyl monomer to be charged is preferably 0.1 to 5 mmol/g, more preferably 0.3 to 3 mmol/g, relative to the total weight of the monomer.

In the suspension copolymerization, the amount of the vinyl monomer containing a group capable of binding to a carboxy group by a dehydration condensation reaction, or the vinyl monomer containing a group convertible, by a reaction such as hydrolysis and the like, to a group capable of binding to a carboxy group by a dehydration condensation to be charged is preferably 0.001 to 1 mmol/g, more preferably 0.005 to 0.5 mmol/g, relative to the total weight of the monomer.

The suspension copolymerization is performed by stirring and emulsifying a mixed lysate with the aforementioned monomers, porogen and polymerization initiator in water containing a dispersion stabilizer dispersed or dissolved therein.

In the present invention, the porogen means a solvent other than water in suspension copolymerization system, and a hydrocarbon and an alcohol are suitably used. Specifically as the hydrocarbon, an aliphatic saturated or unsaturated hydrocarbon or an aromatic hydrocarbon can be used, of which an aliphatic hydrocarbon having from 5 to 12 carbon atoms is preferable, and more preferably, there may be mentioned n-hexane, n-heptane, n-octane, isooctane, undecane, dodecane and the like. In addition, it is preferable to allow an alcohol to coexist in order to increase porosity of the beads obtained at this juncture. As the alcohol according to the invention, an aliphatic alcohol can for example be mentioned, and the number of carbon atoms thereof is preferably from 5 to 9. As such an alcohol, specifically, there can be mentioned 2-ethylhexanol, t-amyl alcohol, nonyl alcohol, 2-octanol, cyclohexanol and the like.

Weight ratio of the hydrocarbon and alcohol to be used as the porogen in the suspension copolymerization can be optionally changed depending on the specific combination of the hydrocarbon and alcohol, and specific surface area of the obtained solid-phase synthesis support can be increased thereby. Preferable blending ratio of the hydrocarbon and alcohol is from 1:9 to 6:4 by weight ratio.

Weight of the porogen at the time of suspension copolymerization is preferably from 0.5 to 2.5 times, more preferably from 0.8 to 2.2 times, further preferably from 1.0 to 2.0 times, based on the total weight of the above-mentioned respective monomers. When this value is larger or smaller than that, specific surface area of the obtained porous resin bead becomes small and quantity of the synthesis reaction product by chemical reaction using the beads becomes small.

According to the present invention, the method itself for carrying out the suspension copolymerization may be carried out by applying a conventionally known method.

The dispersion stabilizer to be used in the suspension copolymerization is not particularly limited, and there can be used a conventionally known hydrophilic protective colloid agents such as polyvinyl alcohol, polyacrylic acid, gelatin, starch, carboxymethylcellulose and the like, slightly soluble powders such as calcium carbonate, magnesium carbonate, calcium phosphate, valium sulfate, calcium sulfate, bentonite and the like, and the like. Although amount of the dispersion stabilizer to be added is not particularly limited, it is preferably from 0.01 to 10% by weight based on the weight of water in the suspension copolymerization system. When this value is smaller, dispersion stability of suspension copolymerization may be spoiled and a large quantity of aggregates may be formed. When this value is larger, a large number of minute beads may be formed.

A polymerization initiator to be used in carrying out the suspension copolymerization is not particularly limited, and there can be used conventionally known peroxides such as dibenzoyl peroxide, dilauroyl peroxide, distearoyl peroxide, 1,1-di(t-butylperoxy)-2-methylcyclohexane, 1,1-di(t-hexylperoxy)-3,3,5-trimethylcyclohexane, 1,1-di(t-hexylperoxy) cyclohexane, 1,1-di(t-butylperoxy)-cyclohexane, di-t-hexyl peroxide, t-butylcumyl peroxide, di-t-butyl peroxide, 1,1,3,3-tetramethylbutylperoxy-2-ethyl hexanoate, t-hexylperoxy-2-ethyl hexanoate, t-butylperoxy-2-ethyl hexanoate, t-butylperoxy-isopropyl monocarbonate and the like, and azo compounds such as 2,2'-azobisisobutyronitrile, 2,2'-azobis-2-methylbutyronitrile, 2,2'-azobis-2,4-dimethylvaleronitrile and the like. The adding amount of the polymerization initiator is not particularly limited, and it is possible to select an appropriate amount by those skilled in the art.

The reaction condition in carrying out suspension copolymerization can be optionally set, and for example, agitation of from 30 minutes to 48 hours at from 60 to 90° C. may be mentioned. The agitation rate is for example from 100 rpm to 1,000 rpm, preferably from 200 rpm to 800 rpm.

The copolymer obtained by the suspension copolymerization may be optionally subjected to washing, drying, classification treatments and the like. In addition, after synthesis of a porous resin bead by suspension copolymerization or the like, a group capable of binding with carboxyl group by dehydration condensation reaction and/or polyethylene glycol unit may be introduced. The introducing method is as described in the foregoing.

The solid-phase support for oligonucleotide synthesis of the present invention loads a cleavable linker having a carboxy group on porous resin beads. The cleavable linker is a compound to be the origin of oligonucleotide synthesis reaction, and is cleaved under the condition of alkalinity and the like with heating to remove the synthesized oligonucleotide from the solid-phase support for oligonucleotide synthesis.

Examples of the cleavable linker having a carboxy group of the solid-phase support for oligonucleotide synthesis of the present invention include, but are not limited to, nucleoside succinyl linkers such as

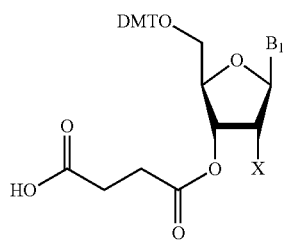

wherein DMT is a dimethoxytrityl group, $B_1$ is a base, and X is H, O-TBDMS, $OCH_3$, or F. Nucleoside linkers bound with various modifying groups and linkers without containing a nucleoside such as universal linkers (e.g., linkers described in U.S. Pat. No. 5,681,945, U.S. Pat. No. 6,653,468, WO 2005/049621 A, and US 2005/0182241 A) can be used.

In the formula, as the base represented by $B_1$, nucleic acid bases such as adenine, guanine, cytosine, thymine, uracil and the like can be mentioned, and the amino group of these nucleic acid bases may be protected by a protecting group such as an acetyl group, an isobutyryl group, a benzoyl group and the like.

As $X^-$, a hydrogen atom, a hydroxyl group, a halogen atom (e.g., fluorine atom, chlorine atom, bromine atom and the like), an alkoxy group having 1 to 20 carbon atoms (e.g., methoxy group and the like), a hydroxyl group protected by a tert-butyldimethylsilyl group etc., and the like can be mentioned.

The loading amount of the cleavable linker of the solid-phase support for oligonucleotide synthesis of the present invention is 1 to 80 µmol/g, preferably 1 to 60 µmol/g, more preferably 3 to 50 µmol/g, further preferably 5 to 45 µmol/g. When the amount of the linker to be loaded is less than 1 µmol/g, the amount of the synthesizable oligonucleotide becomes too small. When the amount of the linker to be loaded exceeds 80 µmol/g, difference from a solid-phase support for oligonucleotide synthesis free of a polyethylene glycol unit is not shown in synthesizability of oligonucleotide.

The loading amount of the cleavable linker of the solid-phase support for oligonucleotide synthesis can be appropriately determined by adjusting the amount of use of the cleavable linker relative to the porous resin beads.

The method of loading the cleavable linker on the solid-phase support for oligonucleotide synthesis of the present invention is not particularly limited. For example, a method including covalently binding, by a dehydration condensation reaction in the presence of a condensing agent, a carboxy group of the cleavable linker and a group capable of binding to a carboxy group by a dehydration condensation reaction of porous resin beads, can be mentioned.

To introduce such group capable of binding to a carboxy group by a dehydration condensation reaction into the porous resin beads of the solid-phase support for oligonucleotide synthesis of the present invention, a method of copolymerizing a vinyl monomer containing a hydroxyl group, such as 2-hydroxyethyl acrylate, 2-hydroxyethyl methacrylate, 2-hydroxypropyl acrylate, 2-hydroxypropyl methacrylate, 4-hydroxybutyl acrylate, 4-hydroxybutyl methacrylate, hydroxystyrene and the like can be mentioned in the case of a hydroxy group. In the case of an amino group, a method of copolymerizing a vinyl monomer containing an amino group, such as aminostyrene, aminomethylstyrene and the like, with a monovinyl monomer and a crosslinkable vinyl monomer can be mentioned.

When the vinyl monomer containing a group capable of binding to a carboxy group by a dehydration condensation reaction is a styrene monomer, a group capable of binding to a carboxy group by a dehydration condensation reaction is preferably present at the para-position relative to the vinyl group. However, it may be the ortho-position or meta-position.

A group capable of binding to a carboxy group by a dehydration condensation reaction, which is contained in the solid-phase support for oligonucleotide synthesis of the present invention, may be produced by once synthesizing, by suspension copolymerization and the like, porous resin beads having a group convertible, by a reaction such as hydrolysis and the like, to a group capable of binding to a carboxy group by a dehydration condensation, and converting, by hydrolysis and the like, to a group capable of binding to a carboxy group by a dehydration condensation reaction.

Examples of the "group convertible, by a reaction such as hydrolysis and the like, to a group capable of binding to a carboxy group by a dehydration condensation" include a straight chain, branched chain or cyclic acyloxy group having 2 to 10 carbon atoms such as an acetoxy group, a benzoyloxy group and the like, a straight chain, branched chain or cyclic acylamino group having 2 to 10 carbon atoms such as an acetylamino group, a benzoylamino group and the like, a straight chain, branched chain or cyclic acyloxy-$C_{1-20}$ alkyl group, wherein the acyl has 2 to 10 carbon atoms, such as an acetoxymethyl group and the like, a straight chain, branched chain or cyclic acylamino-$C_{1-20}$ alkyl group, wherein the acyl has 2 to 10 carbon atoms, such as an acetylaminomethyl group and the like, a halo-$C_{1-20}$ alkyl group such as a chloromethyl group etc., and the like.

Examples of the monovinyl monomer containing a group convertible to a group capable of binding to a carboxy group by a dehydration condensation in the present invention in such production process include acylaminostyrene such as acetylaminostyrene and the like, acyloxystyrene such as acetoxystyrene, ethanoyloxystyrene, benzoyloxystyrene and the like, haloalkylstyrene such as chloromethylstyrene and the like.

When the monovinyl monomer containing a group convertible to a group capable of binding to a carboxy group by a dehydration condensation is a styrene monomer, an acyloxy group, an acylamino group, a haloalkyl group and the like, which are converted to a group capable of binding to a carboxyl group by a dehydration condensation, are preferably present at the para-position relative to the vinyl group. However, it may be the ortho-position or meta-position.

An acyloxy group and an acylamino group in the porous resin beads synthesized by suspension copolymerization and the like can be converted, by a general hydrolysis, for example, a reaction with an inorganic base such as sodium hydroxide and the like in an aqueous alcohol (aqueous ethanol, aqueous methanol), to a group capable of binding to a carboxy group by a dehydration condensation reaction, specifically a hydroxy group and an amino group. In addition, a haloalkyl group can be converted, by a reaction with phthalimide and hydrazine, ammonia, sodium hydroxide and the like, to a group capable of binding to a carboxy group by a dehydration condensation reaction, specifically an aminoalkyl group or a hydroxyalkyl group.

The dehydration condensation reaction can be performed in a solvent inert to the reaction. While such solvent is not particularly limited as long as the reaction proceeds, halogenated hydrocarbon solvents such as dichloromethane, 1,2-dichloroethane, chloroform and the like, aromatic hydrocarbon solvents such as benzene, toluene, xylene and the like, aliphatic hydrocarbon solvents such as pentane, hexane, heptane, octane and the like, nitrile solvents such as acetonitrile and the like can be mentioned. Of these, acetonitrile is preferable.

Examples of the condensing agent include dicyclohexylcarbodiimide (DCC), diisopropylcarbodiimide (DIC), N-ethyl-N'-3-dimethylaminopropylcarbodiimide or hydrochloride thereof (EDC.HCl), (benzotriazol-1-yloxy)tripyrrolidinophosphonium hexafluorophosphate (PyBop), O-(benzotriazol-1-yl)-N,N,N',N'-tetramethyluronium tetrafluoroborate (TBTU), 1-[bis(dimethylamino)methylene]-5-chloro-1H-benzotriazolium-3-oxide hexafluorophosphate (HCTU), O-(benzotriazol-1-yl)-N,N,N',N'-tetramethyluronium hexafluorophosphate (HBTU) and the like. Of these, HBTU, HCTU or dicyclohexylcarbodiimide (DCC) is preferable.

While the reaction temperature is not particularly limited as long as the reaction proceeds, it is preferably −10° C. to 50° C. The reaction time is 30 min to 70 hr.

After the dehydration condensation reaction, preferably, an unreacted group capable of binding to a carboxy group by a dehydration condensation reaction is subjected to capping. Capping can be performed by a conventionally-known method. For example, it is preferably performed by acetylating the unreacted group capable of binding to a carboxy group by a dehydration condensation reaction. While the acetylation reaction is not limited, for example, a solution containing acetic anhydride is preferably added together with a solution containing a basic catalyst (e.g., 1-methylimidazole, pyridine, dimethylaminopyridine etc.) to a solid-phase support.

By the above-mentioned processing, the solid-phase support for oligonucleotide synthesis of the present invention can be obtained.

A conventionally-known method can be applied to oligonucleotide synthesis using the solid-phase support for oligonucleotide synthesis of the present invention.

For example, when a solid-phase support for oligonucleotide synthesis loads a nucleoside linker, nucleoside phosphoramidite is bonded one-by-one so as to give a predetermined base sequence from the 5'-terminus of the nucleoside. This synthesis reaction can be performed by an automatic synthesizer. For example, the reaction is repeated by successively feeding a 5'-OH deprotection agent solution, a nucleoside phosphoramidite solution, an amidite activator solution, an oxidizing agent solution, a capping agent solution, acetonitrile as a washing solution, and the like into the reaction column packed with the solid-phase support for oligonucleotide synthesis. Finally, the desired oligonucleotide can be obtained by cutting the cleavable linker moiety through hydrolysis with an alkali solution, and the like.

The oligonucleotide synthesis using the solid-phase support for oligonucleotide synthesis of the present invention is particularly useful for synthesizing an oligonucleotide, DNA or RNA having a long chain of not less than 20 bases with a decreased loading amount of a cleavable linker (1 to 80 μmol/g).

The present invention is explained in more detail in the following by referring to Examples, which are not to be construed as limitative.

Example 1

Production of Porous Resin Beads

A 500 ml separable flask equipped with a condenser, an agitator and a nitrogen introducing tube was set on a constant temperature water bath and polyvinyl alcohol (2.6 g, manufactured by KURARAY) and distilled water (260 g) were charged therein and stirred at 300 rpm to dissolve the polyvinyl alcohol. Styrene (23.7 g, manufactured by Wako Pure Chemical Industries, Ltd.), p-acetoxystyrene (3.2 g, manufactured by Aldrich), divinylbenzene (21.5 g, content 55%, manufactured by Wako Pure Chemical Industries, Ltd.), polyethylene glycol methyl ether methacrylate (5.4 g, manufactured by Sigma-Aldrich, average Mn 300), 2-ethylhexanol (60.3 g, manufactured by Wako Pure Chemical Industries, Ltd.), isooctane (25.9 g, manufactured by Wako Pure Chemical Industries, Ltd.) and benzoyl peroxide (1.1 g, 25% in water, manufactured by NOF corporation) were mixed and dissolved, and the solution was added thereto. The mixture was stirred (50 rpm) at room temperature under a nitrogen stream, heated to 80° C. to perform suspension copolymerization for 10 hr.

The polymerization product was washed by filtration using distilled water and acetone (manufactured by Wako Pure Chemical Industries) and dispersed in acetone to the total volume of about 1 L. The dispersion was allowed to stand until the precipitate did not become loose even when the dispersion was slanted, and then the supernatant acetone was discarded. Acetone was added again to the precipitate to a total volume of about 1 L and classified by repeating the operations of standing and acetone discharge. By filtering this dispersion and drying same under reduced pressure, porous resin beads comprised of a styrene-divinylbenzene-p-acetoxystyrene-polyethylene glycol methyl ether methacrylate copolymer were obtained.

Then, in a 500 ml flask equipped with a condenser, an agitator and a nitrogen introducing tube were charged a powder of the above-mentioned porous resin beads (20 g) containing the copolymer, ethanol (80 g), distilled water (50 g) and sodium hydroxide (2 g), and the mixture was reacted while stirring at 75° C. for 18 hr. This dispersion solution was neutralized with hydrochloric acid, washed by filtration with distilled water and acetone, and dried under reduced pressure to give porous resin beads comprised of a styrene-divinylbenzene-p-hydroxystyrene-polyethylene glycol methyl ether methacrylate copolymer.

Loading DMT-dT-3'-succinate on Porous Resin Beads

In the proportion of Table 1 (Example 1), porous resin beads, DMT-dT-3'-succinate (manufactured by Beijing OM Chemicals), O-(benzotriazol-1-yl)-N,N,N',N'-tetramethyluronium hexafluorophosphate (HBTU, manufactured by Novabiochem), N,N-diisopropylethylamine (DIPEA, manufactured by Aldrich) and acetonitrile (manufactured by Wako Pure Chemical Industries, Ltd.) were mixed, and the mixture was reacted with stirring at room temperature for 12 hr, washed by filtration with acetonitrile, and dried under reduced pressure.

The porous resin beads were mixed with Cap A (112.5 mL, 20% acetic anhydride/80% acetonitrile), Cap B (12.5 ml, 20% N-methylimidazole/30% pyridine/50% acetonitrile), 4-dimethylaminopyridine (63 mg, manufactured by Aldrich) and acetonitrile (12.5 ml), and the mixture was reacted with stirring at room temperature for 12 hr, washed by filtration with acetonitrile, and dried under reduced pressure to give porous resin beads loaded DMT-dT-3'-succinate. The amount of loaded DMT-dT-3'-succinate was determined by the measurement of absorbance (412 nm) of a DMT group deprotected using a p-toluenesulfonic acid/acetonitrile solution.

The amount of DMT-dT-3'-succinate loaded on the obtained porous resin beads was 7.2 µmol/g.

Synthesis Evaluation of 21 mer RNA Oligonucleotides

The porous resin beads loaded DMT-dT-3'-succinate obtained above were filled in a synthesis column to a synthesis scale of 1 µmol, set on an ABI3400 DNA/RNA synthesizer (manufactured by Applied Biosystems), and RNA oligonucleotides with a 21 mer mixed sequence were synthesized under the conditions of nucleoside phosphoramidite concentration of 0.1 M and DMT-off. The column after synthesis was dried, RNA oligonucleotides were cleaved out from the porous resin beads and the base amino groups was deprotected. The porous resin beads were separated by filter filtration and, from UV absorbance measurement (260 nm) of the filtrate, an OD yield of the RNA oligonucleotides (corresponding to RNA oligonucleotides synthetic quantity) was determined. Then, the filtrate was dried, the 2'-hydroxyl groups of the obtained RNA oligonucleotides were deprotected, and the filtrate was subjected to HPLC measurement (manufactured by Waters) to determine Full-length % (proportion of RNA oligonucleotides having the object sequence length). The results are shown in Table 2.

Comparative Example 1

In the same manner as in Example 1 except that polyethylene glycol methyl ether methacrylate (0 g), styrene (47.0 g), p-acetoxystyrene (4.7 g), divinylbenzene (8.3 g, content 55%), 2-ethylhexanol (55.4 g) and isooctane (23.7 g) were used as the composition for polymerization, porous resin beads comprised of a styrene-divinylbenzene-p-hydroxystyrene copolymer were obtained.

In the same manner as in Example 1 except that the composition of Table 1 (Comparative Example 1) was used, DMT-dT-3'-succinate was loaded on the obtained porous resin beads. The amount of DMT-dT-3'-succinate loaded on the obtained porous resin beads was 11 µmol/g.

In the same manner as in Example 1, RNA oligonutides with a 21 mer mixed sequence were synthesized, and the OD yield and Full-length % of the RNA oligonucleotides were determined. The results are shown in Table 2.

Example 2

In the same manner as in Example 1 except that the composition of Table 1 (Example 2) was used, DMT-dT-3'-succinate was loaded on the porous resin beads obtained in Example 1. The amount of DMT-dT-3'-succinate loaded on the obtained porous resin beads was 45 µmol/g.

The porous resin beads loaded DMT-dT-3'-succinate obtained above were filled in a synthesis column to a synthesis scale of 1 µmol, set on an ABI3400 DNA/RNA synthesizer (manufactured by Applied Biosystems), and DNA oligonucleotides with a 40 mer mixed sequence were synthesized under the conditions of nucleoside phosphoramidite concentration of 0.1 M and DMT-on. The column after synthesis was dried, DNA oligonucleotides were cleaved out from the porous resin beads and the base amino group was deprotected. The porous resin beads were separated by filter filtration and, from UV absorbance measurement (260 nm) of the filtrate, an OD yield of the DNA oligonucleotides (corresponding to DNA oligonucleotides synthetic quantity) was determined. In addition, the filtrate was subjected to HPLC measurement (manufactured by Waters) to determine Full-length % (proportion of DNA oligonucleotides having the object sequence length). The results are shown in Table 2.

Comparative Example 2

In the same manner as in Example 1 except that the composition of Table 1 (Comparative Example 2) was used, DMT-dT-3'-succinate was loaded on the porous resin beads obtained in Comparative Example 1. The amount of DMT-dT-3'-succinate loaded on the obtained porous resin beads was 42 µmol/g.

In the same manner as in Example 2, DNA oligonucleotides with a 40 mer mixed sequence were synthesized, and the OD yield and Full-length % of the DNA oligonucleotides were determined. The results are shown in Table 2.

Comparative Example 3

In the same manner as in Example 1 except that the composition of Table 1 (Comparative Example 3) was used, DMT-dT-3'-succinate was loaded on the porous resin beads obtained in Example 1. The amount of DMT-dT-3'-succinate loaded on the obtained porous resin beads was 108 µmol/g.

In the same manner as in Example 1, RNA oligonucleotides with a 21 mer mixed sequence were synthesized, and the OD yield and Full-length % of the RNA oligonucleotides were determined. The results are shown in Table 2.

Comparative Example 4

In the same manner as in Example 1 except that the composition of Table 1 (Comparative Example 4) was used, DMT-dT-3'-succinate was loaded on the porous resin beads obtained in Comparative Example 1. The amount of DMT-dT-3'-succinate loaded on the obtained porous resin beads was 96 µmol/g.

In the same manner as in Example 1, RNA oligonucleotides with a 21 mer mixed sequence were synthesized, and the OD yield and Full-length % of the RNA oligonucleotides were determined. The results are shown in Table 2.

Example 3

In the same manner as in Example 1 except that styrene (46.9 g, manufactured by Wako Pure Chemical Industries, Ltd.), p-acetoxystyrene (3.7 g, manufactured by Aldrich), divinylbenzene (7.3 g, content 55%, manufactured by Wako Pure Chemical Industries, Ltd.), polyethylene glycol methyl ether methacrylate (3.0 g, manufactured by Sigma-Aldrich, average Mn 950), 2-ethylhexanol (55.4 g, manufactured by Wako Pure Chemical Industries, Ltd.), isooctane (23.7 g, manufactured by Wako Pure Chemical Industries, Ltd.) and benzoyl peroxide (1.2 g, 25% in water, manufactured by NOF corporation) were used as the composition for polymerization, porous resin beads comprised of a styrene-divinylbenzene-p-hydroxystyrene-polyethylene glycol methyl ether methacrylate copolymer were obtained.

In the same manner as in Example 1 except that the composition of Table 1 (Example 3) was used, DMT-dT-3'-succinate was loaded on the obtained porous resin beads. The amount of DMT-dT-3'-succinate loaded on the obtained porous resin beads was 55 μmol/g.

The porous resin beads loaded DMT-dT-3'-succinate obtained above were filled in a synthesis column to a synthesis scale of 1 μmol, set on an ABI3400 DNA/RNA synthesizer (manufactured by Applied Biosystems), and DNA oligonucleotides with a 20 mer mixed sequence were synthesized under the conditions of nucleoside phosphoramidite concentration of 0.1 M and DMT-on. The column after synthesis was dried, DNA oligonucleotides were cleaved out from the porous resin beads and the base amino group was deprotected. The porous resin beads were separated by filter filtration and, from UV absorbance measurement (260 nm) of the filtrate, an OD yield of the DNA oligonucleotides (corresponding to DNA oligonucleotides synthetic quantity) was determined. In addition, the filtrate was subjected to HPLC measurement (manufactured by Waters) to determine Full-length % (proportion of DNA oligonucleotides having the object sequence length). The results are shown in Table 2.

Comparative Example 5

Using the porous resin beads loaded DMT-dT-3'-succinate obtained in Comparative Example 2 and in the same manner as in Example 3, DNA oligonucleotides with a 20 mer mixed sequence were synthesized, and the OD yield and Full-length % of the DNA oligonucleotides were determined. The results are shown in Table 2.

Example 4

Using the porous resin beads loaded DMT-dT-3'-succinate obtained in Example 3 and in the same manner as in Example 2, DNA oligonucleotides with a 40 mer mixed sequence were synthesized, and the OD yield and Full-length % of the DNA oligonucleotides were determined. The results are shown in Table 2.

Example 5

In the same manner as in Example 1 except that the composition of Table 1 (Example 5) was used, DMT-dT-3'-succinate was loaded on the porous resin beads obtained in Example 3. The amount of DMT-dT-3'-succinate loaded on the obtained porous resin beads was 7.1 μmol/g.

In the same manner as in Example 1, RNA oligonucleotides with a 21 mer mixed sequence were synthesized, and the OD yield and Full-length % of the RNA oligonucleotides were determined. The results are shown in Table 2.

Comparative Example 6

In the same manner as in Example 1 except that the composition of Table 1 (Comparative Example 6) was used, DMT-dT-3'-succinate was loaded on the porous resin beads obtained in Comparative Example 1. The amount of DMT-dT-3'-succinate loaded on the obtained porous resin beads was 5.4 μmol/g.

In the same manner as in Example 1, RNA oligonucleotides with a 21 mer mixed sequence were synthesized, and the OD yield and Full-length % of the RNA oligonucleotides were determined. The results are shown in Table 2.

Example 6

Using the porous resin beads loaded DMT-dT-3'-succinate obtained in Example 3 and in the same manner as in Example 1, RNA oligonucleotides with a 21 mer mixed sequence were synthesized, and the OD yield and Full-length % of the RNA oligonucleotides were determined. The results are shown in Table 2.

Comparative Example 7

Using the porous resin beads loaded DMT-dT-3'-succinate obtained in Comparative Example 2 and in the same manner as in Example 1, RNA oligonucleotides with a 21 mer mixed sequence were synthesized, and the OD yield and Full-length % of the RNA oligonucleotides were determined. The results are shown in Table 2.

TABLE 1

Composition and loading amount of DMT-dT-3'-succinate

| | beads (g) | DMT-dT-3'-succinate (mg) | HBTU (mg) | acetonitrile (mL) | DIPEA (μL) | Loading amount (μmol/g) |
|---|---|---|---|---|---|---|
| Ex. 1 | 5.0 | 50 | 25 | 50 | 23 | 7.2 |
| Ex. 2 | 5.0 | 205 | 105 | 50 | 95 | 45 |
| Ex. 3 | 2.0 | 82 | 42 | 20 | 38 | 55 |
| Ex. 4 | 2.0 | 82 | 42 | 20 | 38 | 55 |
| Ex. 5 | 2.0 | 12 | 6 | 20 | 6 | 7.1 |
| Ex. 6 | 2.0 | 82 | 42 | 20 | 38 | 55 |
| Com. Ex. 1 | 5.0 | 268 | 138 | 50 | 123 | 11 |
| Com. Ex. 2 | 5.0 | 165 | 83 | 50 | 77 | 42 |
| Com. Ex. 3 | 5.0 | 490 | 250 | 50 | 230 | 108 |
| Com. Ex. 4 | 5.0 | 410 | 209 | 50 | 192 | 96 |
| Com. Ex. 5 | 5.0 | 165 | 83 | 50 | 77 | 42 |
| Com. Ex. 6 | 5.0 | 25 | 13 | 50 | 11 | 5.4 |
| Com. Ex. 7 | 5.0 | 165 | 83 | 50 | 77 | 42 |

TABLE 2

Synthetic quantity (OD yield) and synthetic purity (Full-Length %) of oligonucleotides

| Synthesized oligonucleotides | No. | number average molecular weight of polyethylene glycol unit | Loading amount (μmol/g) of cleavage linker | OD yield (OD/μmol) | Full-Length (%) |
|---|---|---|---|---|---|
| 20 mer DNA | Ex. 3 | 950 | 55 | 115 | 86.6 |
| | Com. Ex. 5 | 0 | 42 | 97 | 89.0 |
| 40 mer DNA | Ex. 2 | 300 | 45 | 189 | 62.7 |
| | Ex. 4 | 950 | 55 | 199 | 66.3 |
| | Com. Ex. 2 | 0 | 42 | 160 | 62.9 |
| 21 mer RNA | Ex. 1 | 300 | 7.2 | 157 | 55.6 |
| | Com. Ex. 1 | 0 | 11 | 89 | 56.5 |
| | Com. Ex. 3 | 300 | 108 | 119 | 54.5 |
| | Com. Ex. 4 | 0 | 96 | 123 | 58.5 |
| | Ex. 5 | 950 | 7.1 | 165 | 55.7 |
| | Com. Ex. 6 | 0 | 5.4 | 95 | 44.6 |
| | Ex. 6 | 950 | 55 | 191 | 65.5 |
| | Com. Ex. 7 | 0 | 42 | 178 | 65.4 |

INDUSTRIAL APPLICABILITY

Since the solid-phase support for oligonucleotide synthesis of the present invention affords high synthetic quantity and high synthetic purity of long chain oligonucleotide, RNA oligonucleotide and the like even when using a low loading amount of a linker, it enables more efficient synthesis of oligonucleotide than using conventional porous resin beads.

The invention claimed is:

1. A solid-phase support for oligonucleotide synthesis comprising a porous resin bead having a monovinyl monomer unit, a crosslinkable vinyl monomer unit and a polyethylene glycol unit and a cleavable linker loaded on its surface,
    the porous resin bead having a group capable of binding to a carboxy group by a dehydration condensation reaction on its surface,
    the cleavable linker having a carboxy group, wherein the carboxy group of the cleavable linker is bound to the group capable of binding to a carboxy group, by a dehydration condensation reaction, and
    a loading amount of the cleavable linker is 1 to 80 μmol/g relative to the weight of the porous resin bead.

2. The solid-phase support for oligonucleotide synthesis according to claim 1, wherein the monovinyl monomer unit comprises a styrene monomer unit.

3. The solid-phase support for oligonucleotide synthesis according to claim 2, wherein the number average molecular weight of the polyethylene glycol unit is 100 to 10000 and the binding amount thereof is 0.001 to 1 mmol/g relative to the weight of the porous resin bead.

4. The solid-phase support for oligonucleotide synthesis according to claim 3, wherein the group capable of binding to a carboxyl group comprises a hydroxy group or an amino group, and is covalently bonded to the cleavable linker having a carboxyl group.

5. The solid-phase support for oligonucleotide synthesis according to claim 1, wherein the number average molecular weight of the polyethylene glycol unit is 100 to 10000 and the binding amount thereof is 0.001 to 1 mmol/g relative to the weight of the porous resin bead.

6. The solid-phase support for oligonucleotide synthesis according to claim 5, wherein the group capable of binding to a carboxyl group comprises a hydroxy group or an amino group, and is covalently bonded to the cleavable linker having a carboxyl group.

7. The solid-phase support for oligonucleotide synthesis according to claim 1, wherein the group capable of binding to a carboxyl group comprises a hydroxy group or an amino group, and is covalently bonded to the cleavable linker having a carboxyl group.

8. The solid-phase support for oligonucleotide synthesis according to claim 2, wherein the group capable of binding to a carboxyl group comprises a hydroxy group or an amino group, and is covalently bonded to the cleavable linker having a carboxyl group.

9. A method of synthesizing an oligonucleotide, comprising successively binding nucleoside or nucleotide via the cleavable linker by using the solid-phase support for oligonucleotide synthesis according to claim 1 to provide an oligonucleotide.

10. A method of synthesizing an oligonucleotide, comprising successively binding nucleoside or nucleotide via the cleavable linker by using the solid-phase support for oligonucleotide synthesis according to claim 2 to provide an oligonucleotide.

11. A method of synthesizing an oligonucleotide, comprising successively binding nucleoside or nucleotide via the cleavable linker by using the solid-phase support for oligonucleotide synthesis according to claim 3 to provide an oligonucleotide.

12. A method of synthesizing an oligonucleotide, comprising successively binding nucleoside or nucleotide via the cleavable linker by using the solid-phase support for oligonucleotide synthesis according to claim 4 to provide an oligonucleotide.

13. A method of synthesizing an oligonucleotide, comprising successively binding nucleoside or nucleotide via the cleavable linker by using the solid-phase support for oligonucleotide synthesis according to claim 5 to provide an oligonucleotide.

14. A method of synthesizing an oligonucleotide, comprising successively binding nucleoside or nucleotide via the cleavable linker by using the solid-phase support for oligonucleotide synthesis according to claim 6 to provide an oligonucleotide.

15. A method of synthesizing an oligonucleotide, comprising successively binding nucleoside or nucleotide via the cleavable linker by using the solid-phase support for oligonucleotide synthesis according to claim 7 to provide an oligonucleotide.

16. A method of synthesizing an oligonucleotide, comprising successively binding nucleoside or nucleotide via the cleavable linker by using the solid-phase support for oligonucleotide synthesis according to claim 8 to provide an oligonucleotide.

* * * * *